United States Patent [19]

Peschmann et al.

[11] Patent Number: 4,944,448

[45] Date of Patent: Jul. 31, 1990

[54] COMPOSITE ELECTRON BEAM TARGET FOR USE IN X-RAY IMAGING SYSTEM AND METHOD OF MAKING SAME

[75] Inventors: Kristian R. Peschmann, San Francisco; Steve S. Shen, San Bruno, both of Calif.

[73] Assignee: Imatron, Inc., South San Francisco, Calif.

[21] Appl. No.: 861,416

[22] Filed: May 9, 1986

[51] Int. Cl.⁵ .............................. B23K 20/02
[52] U.S. Cl. .................. 228/173.2; 228/44.3; 228/213
[58] Field of Search ............... 228/44.3, 212, 173.2, 228/213, 243; 378/143; 428/661

[56] References Cited

U.S. PATENT DOCUMENTS

| | | | |
|---|---|---|---|
| 3,350,078 | 10/1967 | Shultz et al. | 228/44.3 |
| 3,612,387 | 10/1971 | Rathbun | 228/44.3 |
| 3,735,458 | 5/1973 | Magendans et al. | 228/263.19 |
| 4,145,632 | 3/1979 | Devine, Jr. | 378/144 |
| 4,531,226 | 7/1985 | Peschmann | 378/143 |

*Primary Examiner*—Kenneth J. Ramsey
*Attorney, Agent, or Firm*—Flehr, Hohbach, Test, Albritton & Herbert

[57] ABSTRACT

Disclosed is a composite metal structure of a desired configuration and a method of fabricating the composite metal structure by preshaping at least one metal layer prior to assembly of the metal layers in a die of a second preshape configuration. Following brazing of the metal layers while in the die, the brazed structure is removed from the die and springs to the final desired configuration. The process has proved to be particularly useful in fabricating composite electron beam targets for use in X-ray scanners.

11 Claims, 3 Drawing Sheets

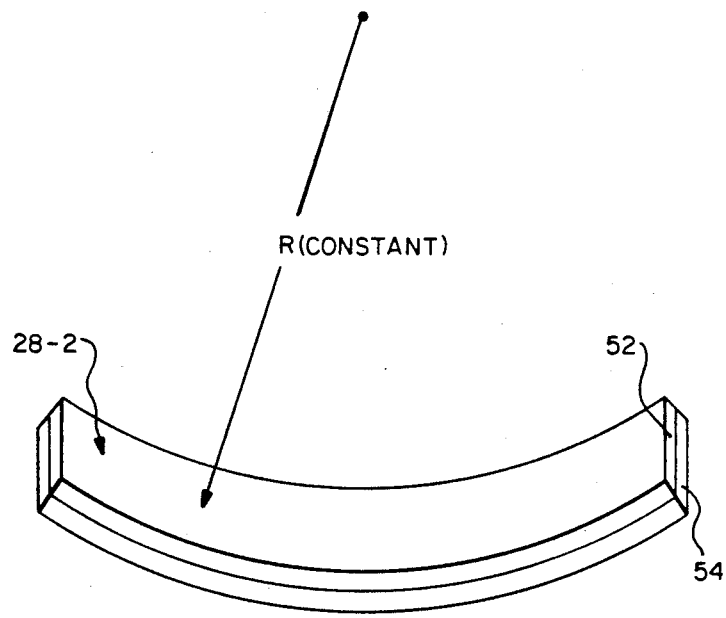
FIG.—5
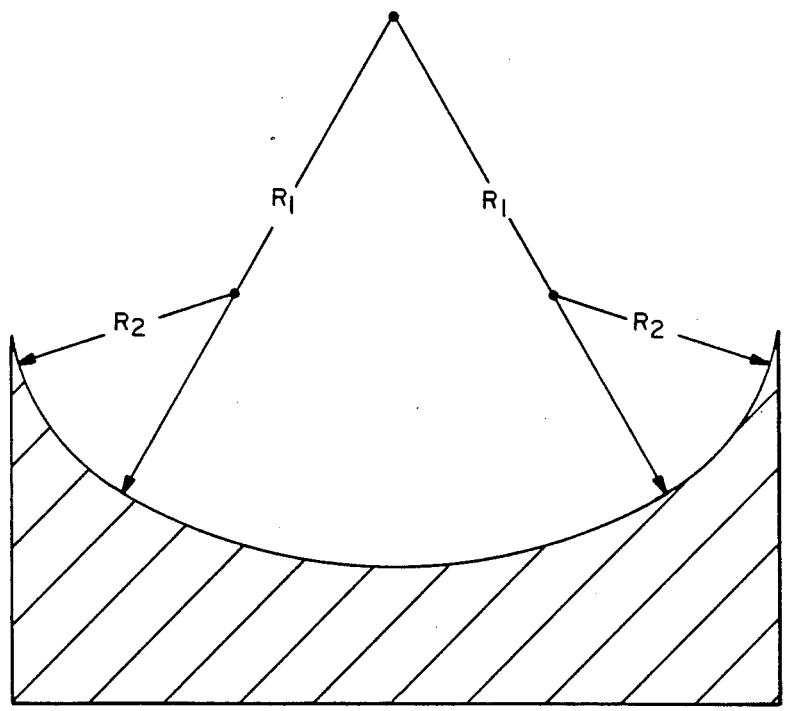
FIG.—6

COMPOSITE ELECTRON BEAM TARGET FOR USE IN X-RAY IMAGING SYSTEM AND METHOD OF MAKING SAME

BACKGROUND OF THE INVENTION

This invention relates generally to a high speed multiple section computed-tomographic (CT) medical scanning system, and more particularly the invention relates to an electron beam target structure for use therein.

Disclosed in U.S. Pat. No. 4,352,021 is a high speed X-ray scanning system in which the X-ray source and the X-ray detectors are stationary and a plurality of fan beams of radiation is generated by sweeping an electron beam across a plurality of targets arcuately arranged whereby each target generates radiation fan beams.

The electronic scanning system incorporates a single electron beam tube. The electron beam is deflected by suitable mangetic and/or electric fields to produce a movable X-ray source on one of four adjacent semi-circular target rings to provide scanning fan beams that can be used to image an entire volume of tissue in multiple sections. Such an electronic scanning system is vastly superior in speed to the mechanical scanning systems in the prior art refences in U.S. Pat. No. 4,352,021. Fraction-of-a-second scan time of a volume can be achieved as compared to one or more seconds required for the mechanical scan of a single section. The system eliminates the need for moving parts that require high precision and alignment. In addition, elaborate systems of sliding electrical contacts are eliminated. The scanner is an improvement over that shown and described in U.S. Pat. No. 4,158,142, in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 432 detectors each, providing a total of 864 detectors. The angular separation of two adjacent detectors is in the order of 0.5 degrees resulting in very high resolution. The scanning system is provided with collimators both for the X-ray source and for the detectors. The source collimator provides a fan-shaped beam 30° opening angle. The detector collimators provide interchangeable options: dual section detector arrays, single section detector arrays and high resolution single section detector arrays. A variety of scanning modes can be selected with up to eight sections being scanned at a rate of at least one scan per second.

A problem encountered in the described system results from the high temperatures of the electron beam target which can cause burnout or degraded X-ray sources. Typically; the electron beam current is one ampere at 120 Kv, and the beam power of 120 kilowatt, concentrated in a focus of a typical area of one mm by 10 mm, heats the target surface temperature to an extremely high value, even when this spot is moved along the targets with high speed.

U.S. Pat. No. 4,531,226 discloses a target structure including an arcuate frame and a plurality of support brackets extending therefrom. Each support bracket has at least one recessed portion including one inclined surface at an angle required by the surface of an electron beam target. Since the bracket is arcuate the inclined surface is in fact of conical shape. The electron beam target comprises a member having a planar surface. The member is supported in the recessed portion with the planar surface engaging the inclined recessed wall. Fastening means engages the target and maintains the planar surface of the target in forced engagement with the inclined recessed surface. The shape of the target takes on the conical shape of the inclined bracket surface. The fastening means accommodates targets of various thicknesses and allows for thermal expansion of the targets. Further, each target can be readily replaced in the field. Advantageously, in a multiple target arrangement each target shields the support bracket from the electron beam thereby reducing heat and minimizing damage to the bracket.

The '226 patent describes each target segment as being a solid tungsten sheet or a mounting substrate such as OFHC copper on which a tungsten layer is deposited by plasma spray or to which a tungsten sheet is brazed. Other X-ray emitting surface material such as tantalum and molybdenum may be used. However, a problem arises in attempting to braze the tungsten or molybdenum sheets to a supporting substrate and then forming the composite structure to a desired configuration.

Another object of the present invention is an improved composite electron beam target for use in an X-ray scanner.

Still another object of the invention is a method of making a composite electron beam target having a desired configuration.

A feature of the invention is preforming at least one individual metal layer and joining the layers by brasing in a die clamp.

Briefly, a composite structure is fabricated in accordance with the invention by preforming a substrate in a suitable mold. The preformed substrate and a layer of target material are then brazed in a die having a second preformed shape.

In accordance with a feature of the invention the dies have bi-radial cylindrical shapes to overcome the "flattening out" of the preformed substrate and the brazed composite sheets at the ends. Thus when the brazing die is opened the layers of brazed material will spring to the desired configuration and will maintain the configuration during usage.

In an electron beam target for producing a high brightness focus and emitting electrons, at least one of the layers is a refractory metal such as tungsten, tungsten alloy, molybdenum, or molybdenum alloy and the substrate material may be OFHC copper or a titanium-zirconium-molybdenum alloy. Because of high tungsten price, poor machining properties, brittleness, and high density those targets are often layered composites where only the active layer is tungsten (or tungsten alloy). The adjoined substrate material is selected in respect to the required properties for the joining technologies available and according to other desired properties like heat conductance, weight, machining properties, etc. (classical joining technologies are, among others, forging and brazing). The problems of brazing are numerous, dealing with differential expansion, wetting characteristics, as well as temperature stablility and cost of the brazing alloy, and more.

The invention and objects and feature thereof will be more readily apparent from the following detailed description and appended claims when taken with the drawing.

BRIEF DESCRIPTION OF THE DRAWING

FIG. 5 is a perspective view of one target segment of FIG. 4 in accordance with the present invention.

FIG. 6 is a section view of a die useful in fabricating the target segment of FIG. 5 in accordance with the invention.

DETAILED DESCRIPTION OF ILLUSTRATIVE EMBODIMENT

Figure 1:
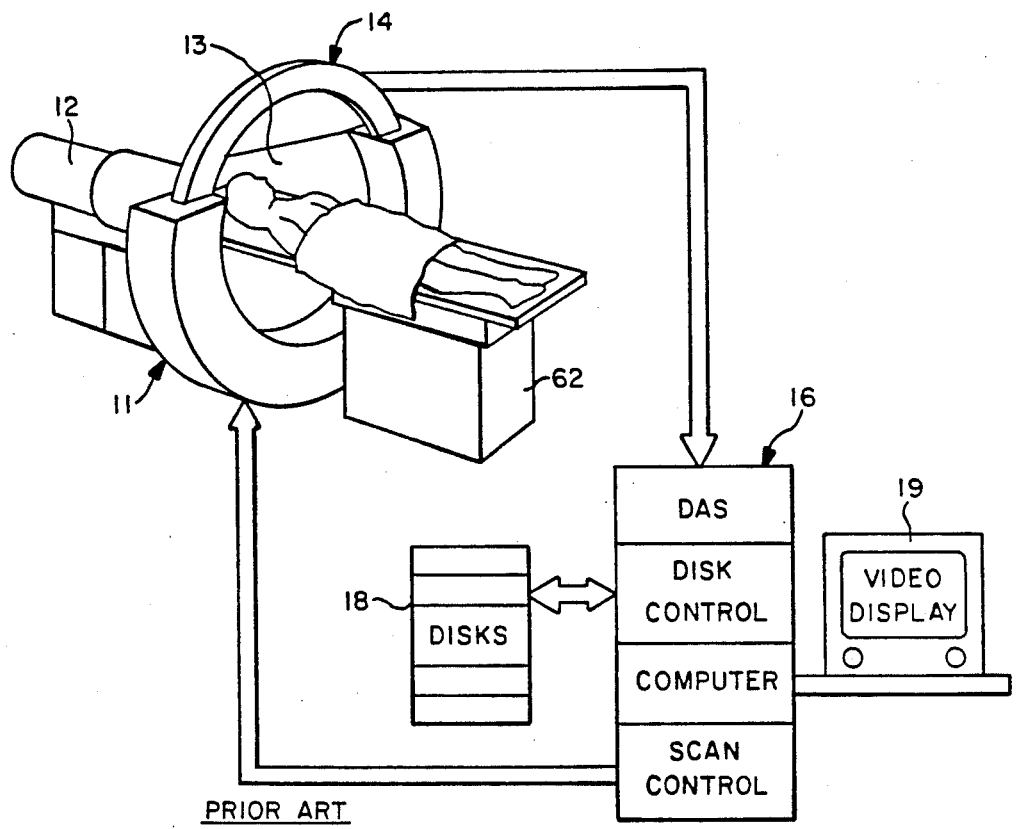
FIG. 1 is a schematic diagram partly in perspective showing a computed tomographic X-ray transmission scanning system employing multiple electron beam targets.

Referring to FIG. 1, the system of U.S. Pat. No. 4,352,021 is seen to include three major components: a scan tube 11 including a cylindrical portion 12, and a semi-circular conical portion 13; a detector array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Figure 2:
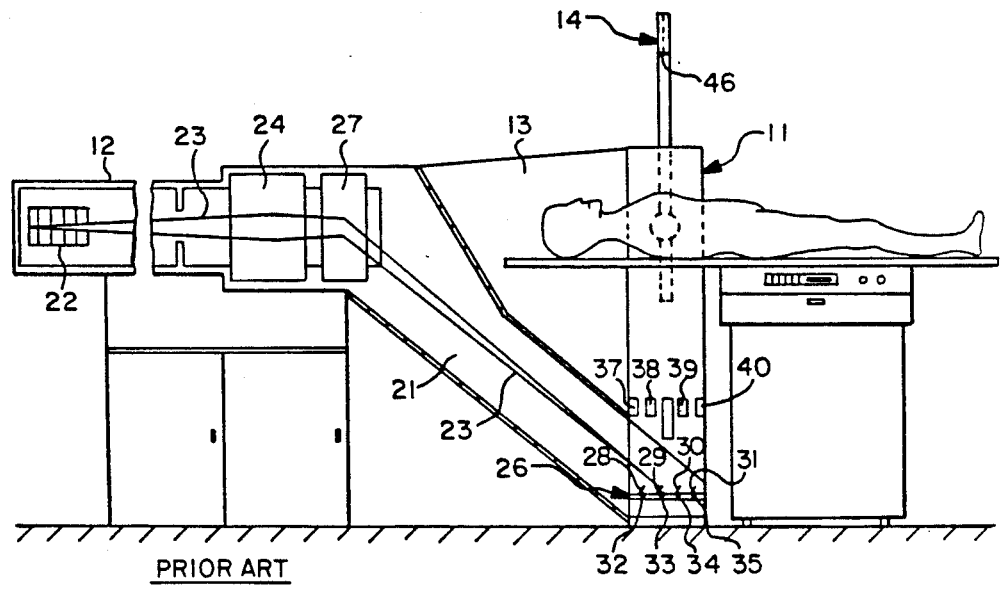
FIG. 2 is a cross section view of the system of FIG. 1.
Figure 3:
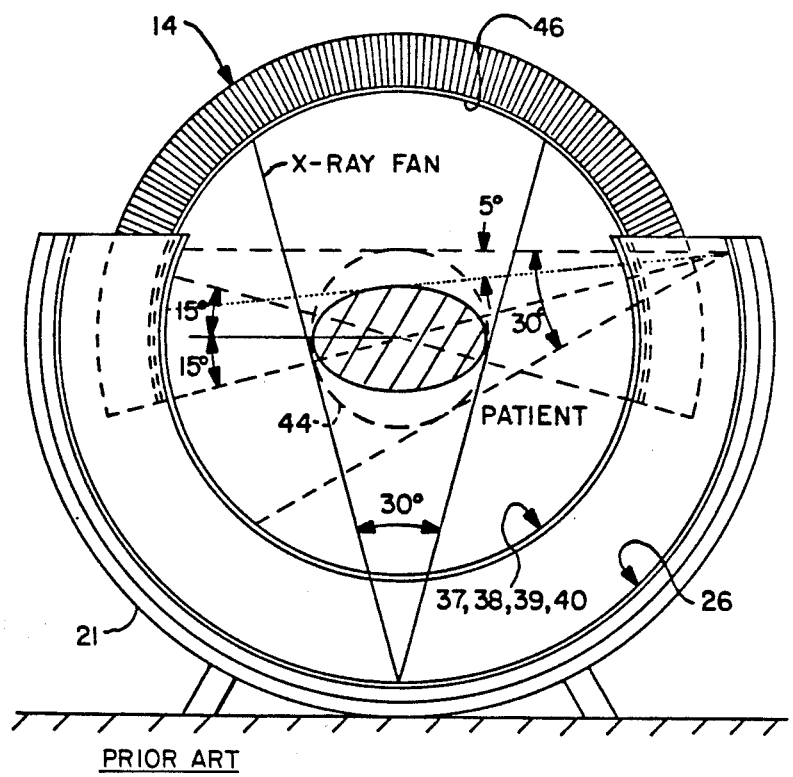
FIG. 3 is an end view of the system of FIG. 1.

Referring more particularly to FIGS. 2 and 3, the scanning system and detection system is shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is passed through a detector collimator 46 and is detected by the curved detector array and the measured values are utilized to reconstruct a tomographic image of the region 44.

Figure 4:
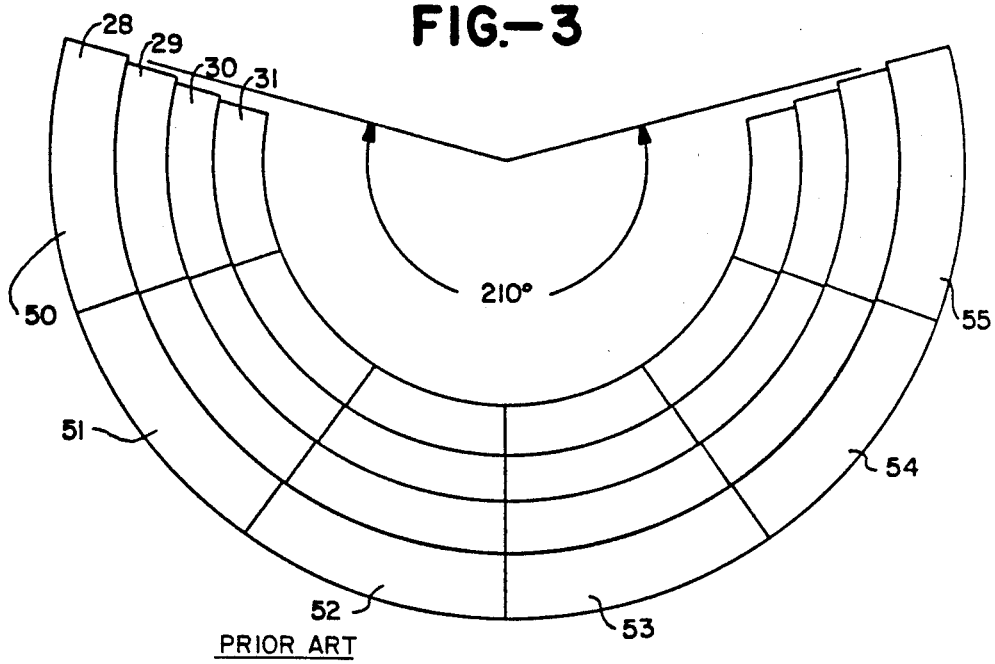
FIG. 4 is a perspective view of electron beam targets in the system of FIG. 1.

FIG. 4 is a perspective view if the targets 28-31 each of which is arouate in configuration (e.g 210°) and comprises a plurality of segments such as the six-segments 28-1 through 28-6 for the target 28. Each segment may be solid tungsten sheet or a mounting substrate such as OFHC copper on which a tungsten layer is deposited by plasma spray or to which a tungsten sheet is brazed. Other X-ray emitting surface material, such as tungsten and molybdenum, may be used.

A difficulty encountered in the prior art in the fabrication of composite target segments lies in the brazing of the target material to a supporting substrate while maintaining the desired target configuration. Attempts at shaping the target after the composite material is fabricated is difficult because of stressed induced in the brazed layers.

In accordance with the present invention it has been discovered that a desired final configuration can be achieved by preshaping at least the supporting substrate. The preshaped substrate and the layer of target material are then brazed together in a particularly shaped die. After the brazing process it has been found that the composite structure will spring to a desired configuration upon removal from the die.

FIG. 5 is a perspective view of one target segment 28-2 of FIG. 4 and illustrates the composite structure including a rolled refractory metal 52 such as tungsten or a tungsten alloy after brazing to a supporting substrate 54 such as molybdenum or a molybdenum alloy. The inner concave surface layer of the target structure 28-2 conforms to the conical shape of the inclined surface of the "arcuate bracket".

In accordance with the invention the desired configuration is realized for the final composite sturcture by first preshaping at least the substrate in a suitable die. The performing is performed in a cold forming die, so that after release of elastic deformation the preformed part fits appropriately in a brazing die. The preformed substrate and layer of target material are then stacked in a bi-radial brazing die and kept in this die under pressure in the brazing furnace. All layers get softer in the furnace so that they confers to the shape of the brazing die. After the brazing and cool down of the materials, the brazing die is opened and the brazed structure assumes the final desired configuration. It has been discovered that by accentuating the curvature of the surfaces of the two metal layers prior to brazing and also during the brazing, the biradial cylindrical shape compensates for the flattening out of the brazed structure upon removal from the die. That is, upon opening the brazing die the layered brazed material will spring into the desired shape.

In one embodiment of an X-ray target with a concave tungsten alloy surface of 175 inch curvature, a substrate layer consisting of a 14 inch long, 1.6 wide, and 0.1 inch thick strip of molybdenum alloy MT104, supplied by GTE, was deformed cold in a two-piece steel die with a radius of 11 inches. A brazing die made from graphite (AT) grade, supplied by Union Carbide with a bi-radial shape ($R_1=65$ inch, $R_2=40$ inch) was then loaded side by side with two "sandwiches", each consisting of the cold formed piece of MT104, a foil of 1.5 mil thick alloy of silver and Palladium (palsil-10, supplied by GTE-Wesgo), and of a strip of rolled tungsten-rhenium alloy, 14 inch long, 1.6 inch wide and 0.025 inch thick, supplied by SDC (Schwarzkopf Development Corporation, Holliston, Mass.).

The graphite die was then loaded into a vacuum furnace with graphite heating elements, and a weight of 40 lbs. was used to compress the graphite die. The temperature in the furnace was then slowly raised to 2000° F. and kept there for 10 minutes. After controlled cooling down, the graphite die was released and a brazed sandwich of cylindrical shape with radius 175 inches obtained.

The invention is applicable to any composite structure comprising at least two brazed metgal sheets. The method of fabricating a composite electron beam target structure in accordance with the invention permits the fabrication of targets having the required configuration for the required application in an X-ray scanner. Further, rolled tungsten can be used in fabricating the electron beam target thus reducing cost. By reinforcing the target, the shape does not change during high power beam input. Additionally, the average bulk temperature and hence the thermo-expansion of the targets at a given power input is reduced.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A method of fabricating a composite structure including at least two metal sheets brazed together comprising the steps of preforming at least one of said metal sheets, assembling said metal sheets in a die having a preselected shape, and brazing the assembled metal sheets while in said die.

2. The method as defined by claim 1 wherein the final cross sectional configuration of the composite structure is defined by a radius, $R_1$, and wherein said die has a cross section in which a major central portion is defined by said radius, $R_1$, and edge portions are defined by a radius, $R_2$, which is shorter than $R_1$, the brazed composite structure springing to the desired configuration upon removal from the die.

3. The method as defined by claim 2 wherein said final configuration comprises a conical shape.

4. A method of fabricating a composite electron beam structure for use in computerized tomography, the structure conforming generally to a conical shape, said method comprising the steps of providing a die having a cross section in which a major central portion is defined by a radius, $R_1$, of the desired conical shape and edge portions are defined by a radius, $R_2$, which is shorter than $R_1$, preforming a substrate material, assembling a layer of target material on said substrate in said die, and brazing said target material to said substrate while in said die, the brazed composite structure springing to the desired conical shape upon removal from the die.

5. The method as defined by claim 4 wherein said target materisl comprises tungsten.

6. The method as defined by claim 4 wherein said target material comprises rolled tungsten.

7. The method as defined by claim 4 wherein said target material comprises tungsten alloy.

8. The method as defined by claim 4 wherein said substrate material comprises molybdenum.

9. The method as defined by claim 8 wherein said substrate material comprises a molybdenum alloy.

10. The method as defined by claim 4 and further including the step of preforming said layer of target material.

11. A composite metal structure of metal sheets, brazed together of a desired configuration, said composite structure being fabricated by preforming at least one of two metal sheets, assembling said two metal sheets in a die having a preselected surface shape, and brazing said two metal sheets together while in said die, the cross section of the final composite structure configuration being defined by a radius, $R_1$, said die having a cross-section in which a major central portion is defined by said radius, $R_1$, and edge portions are defined by a radius, $R_2$, which is shorter than $R_1$, whereby said composite structure springs to said desired configuration following the brazing and removal from said die.

* * * * *